United States Patent [19]

Göthel et al.

[11] 4,041,080

[45] Aug. 9, 1977

[54] PROCESS FOR THE PRODUCTION OF PRIMARY AMINES

[75] Inventors: Herbert Göthel, Oberhausen-Holten; Boy Cornils; Hans Feichtinger, both of Dinslaken; Hans Tummes, Oberhausen-Sterkrade-Nord; Jurgen Falbe, Dinslaken, all of Germany

[73] Assignee: Ruhrchemie Aktiengesellschaft, Oberhausen, Germany

[21] Appl. No.: 417,590

[22] Filed: Nov. 20, 1973

Related U.S. Application Data

[63] Continuation of Ser. No. 182,773, Sept. 22, 1971, abandoned.

[30] Foreign Application Priority Data

Oct. 3, 1970 Germany .............................. 2048750

[51] Int. Cl.² ............................................. C07C 85/02
[52] U.S. Cl. ................................................ 260/585 B

[58] Field of Search .................................. 260/585 B

[56] References Cited

U.S. PATENT DOCUMENTS

| 2,452,602 | 11/1948 | Robinson et al. | 260/585 C X |
| 2,518,659 | 8/1950 | Brimer et al. | 260/585 C X |
| 3,346,640 | 10/1967 | Guyer et al. | 260/585 C X |
| 3,483,253 | 12/1969 | Adam et al. | 260/585 C X |
| 3,520,933 | 7/1970 | Adam et al. | 260/585 C |
| 3,535,379 | 10/1970 | Besson et al. | 260/585 C X |
| 3,597,438 | 8/1971 | Brake | 260/585 C X |

Primary Examiner—Paul F. Shaver
Attorney, Agent, or Firm—Bierman & Bierman

[57] ABSTRACT

A process for the production of primary amines which comprises reacting compounds containing carbonyl groups with ammonia at a specific temperature, separating the water formed therefrom and hydrogenating the resulting product under pressure.

11 Claims, 1 Drawing Figure

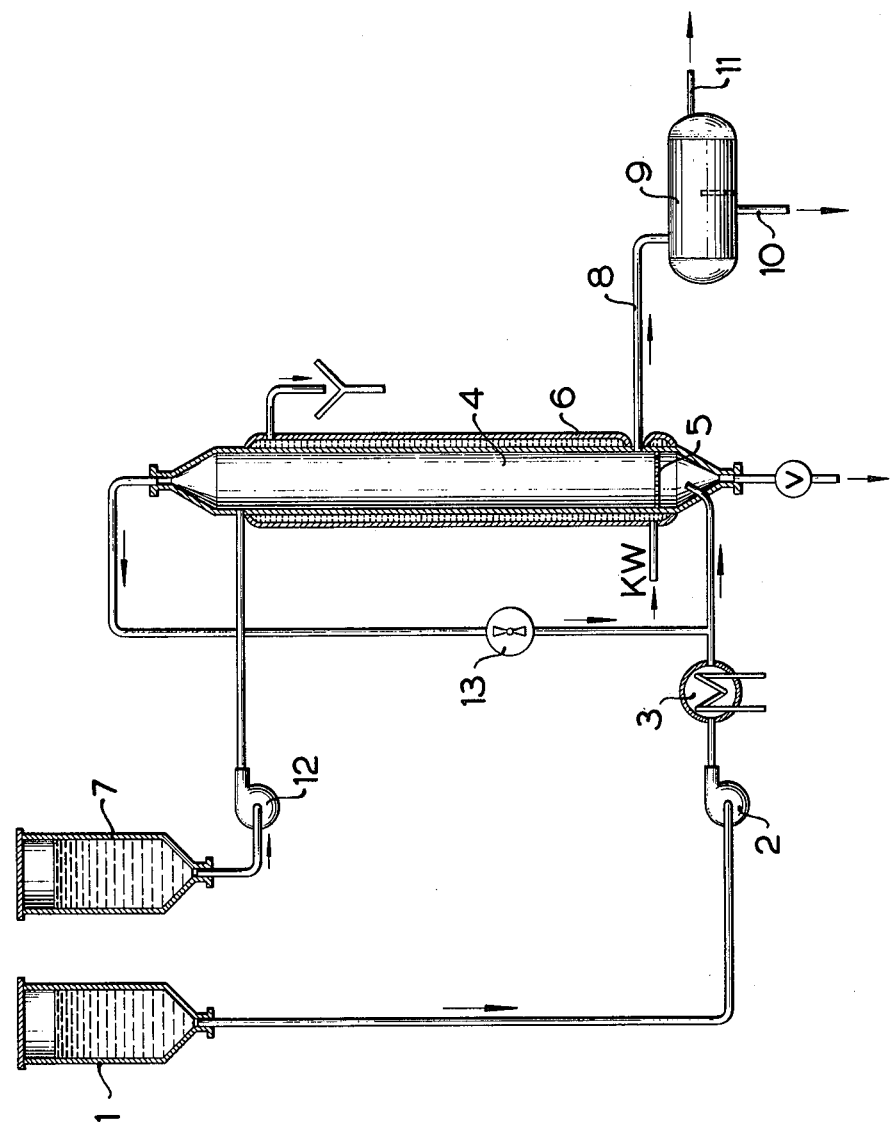

PROCESS FOR THE PRODUCTION OF PRIMARY AMINES

This is a continuation of application Ser. No. 182,773 filed Sept. 22, 1971 now abandoned and which claims the priority of German P 20 48 750.7 filed Oct. 3, 1970.

It is known to produce amines by reaction of saturated and unsaturated aldehydes with ammonia and hydrogen (see Houben-Weyl, Vol. 11/1, page 602 ff). The reductive amination reaction is effected in a pressure-range between 70 and 330 atmospheres gauge and at temperatures ranging between 80° and 200° C. Dehydrogenation/hydrogenation catalysts containing metals of Groups VIII of the periodic table, preferably nickel or cobalt, are used as catalysts. The said catalysts may be activated by the addition of thorium or copper oxide as well as of baryum chromite or oxides of metals of Group V and VI of the periodic table, especially chrome.

Special combinations of nickel and/or cobalt and chrome with added non-volatile mineral acids, which can be converted to insoluble anhydrides or polyacids have more recently been used as catalysts. Furthermore, the conversion as well as the selectivity of the reaction can be increased with catalysts containing 5 to 80% by weight cobalt and/or nickel and/or chrome and/or silver and 0.1 to 10% by weight copper and/or manganese. The catalysts are stabilized by the content of pyro- and polyacids.

The drawback of the reductive amination of aldehydes or ketones consists in the relatively poor volume-time-output of the catalyst. It is therefore an object of the invention to provide a method of producing the desired amine with high volume-time-output in an economical manner. This objective can be achieved by increasing the catalytic conversion reaction. This is done by dividing the reaction under pressure of the compounds containing carbonyl groups with ammonia and hydrogen into several process stages, some of which can be performed outside of the pressure reactor and thus do not burden the catalytic process.

The process for the production of primary amines by conversion of compounds containing carbonyl groups with ammonia and catalytic hydrogenation of the resulting reaction product in presence of cobalt and/or nickel containing catalysts, according to the invention, comprises reacting, in a first stage, compounds containing carbonyl groups with ammonia at a temperature ranging between 15° to 80° C., preferably 15° to 30° C.; separating, in a second stage, water formed during the reaction of the first stage, and hydrogenating, in a third stage, the resulting organic reaction product in known manner under increased pressure in presence of ammonia and a catalyst.

The reaction of the compounds containing carbonyl groups can be performed in presence of an inert solvent, for instance, a hydrocarbon fraction. Especially well suited are aliphatic hydrocarbons having 5 to 10 carbon atoms.

The first stage of the process is advantageously carried out under pressures up to 15 atmosphere gauge, preferably under atmospheric pressure.

It is convenient to maintain a molar ratio of the compounds containing carbonyl groups to ammonia between 1 : 1.3 and 1 : 1.8 in the first stage.

Owing to the separation of the reaction water formed during the first stage of the process, the formation of a water phase in the catalytic hydrogenation stage is avoided, which otherwise would heavily burden the catalyst so that the throughput would be kept small.

From German Pat. No. 936,211 and U.S. Pat. No. 2,809,995, it is known to admix an aldehyde and ammonia in a preceding stage in presence of a solvent at a temperature below 0° C. and to thereafter convert the resulting addition product in presence of a catalyst to the corresponding amine, thus preventing aldol condensations which lead to a decrease of the amine formation.

According to U.S. Pat. No. 2,219,879, condensation products of butyr-aldehyde and ammonia are formed at temperatures ranging between 10° and 30° C., preferably 10° and 12° C. in presence of alcohols and thereafter catalytically hydrogenated at ambient temperature.

In the aforementioned known processes the water formed during the contact between aldehyde and ammonia is present during the catalytic hydrogenation, thus causing the above indicated drawbacks.

In the process described in German Pat. No. 921,864 the water formed during the reaction of the aldehydes and ammonia is azeotropically separated, but this process is involved with the preparation of nitrogen containing condensation products and resin-like compounds, aminating hydrogenation resulting in the formation of primary amines is not intended by these references.

From the above known measures which were carried out to avoid aldol condensation or to obtain nitrogen containing condensation products, it could not be concluded that an increase of the throughput can be obtained with the process of aminating hydrogenation according to the invention. It was therefore highly surprising that with the process according to the invention, the reductive amination can be performed with the 6 to 10 fold throughput at the catalyst.

Any compounds containing carbonyl groups can be used as starting materials for the process of the invention. These are especially well suited for the conversion of aliphatic aldehydes having 2 to about 15 carbon atoms, as for instance acetaldehyde, propionaldehyde, n- and i-butyraldehyde, isononylaldehyde and so on. Furthermore, aliphatic aldehydes substituted by phenyl radicals, as for instance phenylpropanal, as well as cycloaliphatic aldehydes, are suitable. The resulting nitrogen containing condensation products comprising generally hydramides are, despite the fact that they often have high viscosities, fluid enough to allow the separation of reaction water. In many cases, however, addition of diluents or entraining agents is indicated in order to decrease the viscosity and to obtain complete separation of water. Suitable diluents are, for instance, hydrocarbon fractions, which boil higher or lower than the desired amines and the starting aldehydes respectively.

The following pressure hydrogenation is carried through in conventional manner in presence of ammonia with suitable catalysts known in the art. Especially well suited are commercially available cobalt and/or nickel containing carrier catalysts which, besides the said metals, may contain conventional activators. The produced amines are separated by distillation from the starting materials and conversion products. The desired primary amines are obtained in high yields and high purity.

The different process stages may be performed in any suitable device in a discontinuous or continuous procedure. Especially well suited is a process in which the first reaction stage is performed in a bubble column reactor wherein the liquid and the gaseous ammonia are contacted in a concurrent or countercurrent flow, respectively. It may, however, also be conducted in a flow-tube or under mechanical agitation in a mixing vessel. The hydrogenation stage may be conducted in a trickling device or a slurry operation. The parts of the plant, in which exothermic reactions take place, are provided with cooling means in order to eliminate the heat of reaction. Favorable conditions of heat transfer are given at countercurrent flow of the gas-liquid fluidized system. The throughput-efficiency of the following catalytic process is raised since part of the reaction heat of the entire process is already eliminated in the gas-liquid fluidized system.

In the accompanying drawing, constituting a part hereof, and in which like reference characters indicate like parts, the single FIGURE shows a device for the performance of the process according to the invention.

Gaseous ammonia from a pressure vessel 1 is conveyed with the aid of a pump 2 through a heat exchanger 3 and introduced into a vertically arranged reactor 4 through a sieve plate 5. The reactor 4 is equipped with a cooling jacket 6 for the elimination of the reaction heat. The aldehyde to be converted is continuously conveyed from a supply vessel 7 by means of a pump 12 and introduced into the reactor 4 countercurrently to the gas flow. Thereby intimate admixture and instantaneous reaction of aldehyde and ammonia occurs. Excess ammonia exiting at the head of the reactor is recirculated by means of blower 13. Above sieve plate 5 is provided an outlet tube 8 leading to a settling tank 9, wherein the liquid nitrogen containing organic phase is separated from the aqueous phase, which is quickly formed during the condensation. The latter is continuously drawn off through line 10 while the water-free organic phase is introduced through a line 11 to a not shown device for the reductive amination, which is likewise continuously performed.

The following Examples 1 to 3 are given to further illustrate the practice of the invention. Example 4 shows a comparison test.

EXAMPLE 1

25 to 30 l/h of a mixture of 80% by weight isononylaldehyde (3,5,5-trimethylhexanal) and 20% by weight isooctane were introduced by means of pump 12 into reaction vessel 4 consisting of a steel tube of 100 mm internal width and a height of 3780 mm of the area of the bubble column equipped with cooling jacket 6, as shown in the drawing. Simultaneously, 3.0 kg/h ammonia were conveyed by pump 2 via evaporator 3 and introduced into reactor 4 finely divided by sieve plate 5. Non-reacted ammonia was recirculated by means of gas circulation pump 13. The amount of freshly introduced ammonia (via pump 2) and recirculated ammonia (via pump 13), respectively, was adjusted in such manner that the molar ratio of the starting aldehyde to ammonia ranged between 1 : 1.3 and 1 : 1.8. The reaction proceeds between 20° and 22° C. The reaction mixture is continuously drawn off through outlet tube 8, and separates in settling tank 9 into an organic phase of aldimine and isooctane and an aqueous phase. The organic phase has a viscosity of 20 to 35 cSt and a water content of 1.6% by weight, the residual content of unreacted amine ranges between 0.5 and 8.0% by weight depending upon the respective reaction conditions.

The organic phase is introduced through line 11 into a hydrogenation reactor with 20 l contact volume and converted in the presence of a commercial hydrogenation catalyst under a hydrogen pressure of 100 atmospheres gauge, at a reaction temperature of 115° C. with a molar ratio of the charging stock to $NH_3$ of 1 : 4. The reaction mixture of the hydrogenation contains 20% by weight isooctane besides 78% by weight primary $C_9$-amine and 2% by weight higher amines and condensation products of amines and aldehydes. If alcohol containing aldehydes are used as starting materials for the process according to the invention, the reaction product contains corresponding amounts of alcohol.

The distillative working up of the hydrogen product to obtain $C_9$- amine is performed in conventional manner.

EXAMPLE 2

1.1 l/h (890 g/h) n-butyraldehyde are introduced into reactor 4 from vessel 7 as described in Example 1, while 415 l/h gaseous ammonia enter reactor 4 through sieve plate 5. The resulting condensation product flows through tube 8 into the settling tank 9. The temperature of the product amounts to 21°, while the cooling water has a temperature of 20° C. The organic phase exiting from settling tank 9 has a density $d_{20}$ of 0.919, a refraction index of 1.4612, and a viscosity $V_{20}$ of 92 cSt. This clear product still contains 7.9% by weight dissolved water, 150 g/h water are drained off through line 10.

850 g/h of the reaction product are treated as described in Example 1 in a pressure reactor with 715 g/h ammonia at 120° C under a hydrogen pressure of 120 atmosphere gauge in the presence of a cobalt catalyst consisting of 100 parts by weight Co, 30 parts by weight MnO, 10 parts by weight MgO, and 60 parts by weight of diatomaceous earth as a carrier. After separation of ammonia and residual water by distillation, 865 g/h n-butylamine were obtained, having a gas-chromatographically determined purity of 99.4%.

EXAMPLE 3

41.5 kg/h of a mixture of 80 parts by weight isononylaldimine and 20 parts by weight isooctane obtained by reaction of isononylaldehyde and ammonia is presence of isooctane according to Example 1 are introduced through line 11 into a hydrogenation reactor of 80 l contact volume, wherein it is converted under a hydrogen pressure of 100 atmosphere gauge at a reaction temperature of 126° C. with a molar ratio of the charging stock to $NH_3$ of 1 : 4 in presence of the cobalt catalyst described in Example 2. The resulting hydrogenation product contains besides 20% by weight isooctane 77% by weight primary isononylamine and 3% by weight higher amines and byproducts originating from reactions between aldehyde and amine.

EXAMPLE 4

6.7 kg/h isononylaldehyde are introduced into a reactor of 80 l contact volume, where the aldehyde is converted at a ammonia pressure of 100 atmospheres gauge, a reactor temperature of 126° C. and a molar ratio of the isononylaldehyde to ammonia of 1 : 8 in presence of a cobalt catalyst as described in Example 2. The product resulting from the hydrogenating amination contained 4% by weight water, 91% by weight primary isononylamine and 5% by weight higher amines and condensation products of aldehyde and amines.

If an increased amount of isononylaldehyde-charging stock is treated per hour under the hereinbefore mentioned conditions, the yield of primary isononylaldehyde is considerably decreased owing to the formation of Schiff's base. If, for instance, the isononylaldehyde-charging stock amounts to 33 kg/h, which nearly corresponds to the charging stock of isononylaldimine of Example 3, a reaction product consisting generally of the corresponding Schiff's base and only 10% by weight isononylamine is obtained.

What is claimed is:

1. In a process for the production of a primary amine by conversion at a first pressure of a compound selected from the group consisting of an aliphatic aldehyde having 2–15 carbon atoms, a cycloaliphatic aldehyde and an aryl aldehyde, said aldehydes containing no other functional group other than a carbonyl group, with ammonia to produce a reaction product and catalytic hydrogenation of said reaction product in the presence of a catalyst, wherein the catalyst contains cobalt, nickel, or a mixture thereof, the improvement which consists essentially of reacting said compounds with ammonia at a temperature of between about 15° and 80° C. at a pressure of between about 1 and 15 atmospheres, separating the water formed during the reaction from said reaction product and hydrogenating said product under a second pressure, said second pressure being greater than said first pressure.

2. A process according to claim 1 wherein said temperature is 15° to 30° C.

3. A process according to claim 1 wherein said conversion takes place in the presence of an inert solvent.

4. A process according to claim 3 wherein the inert solvent is a hydrocarbon fraction.

5. A process according to claim 4 wherein said first pressure is up to 15 atmospheres gauge.

6. A process according to claim 5 wherein said pressure is atmospheric pressure.

7. A process according to claim 1 wherein the molar ratio of said compounds to said ammonia is from 1 : 1.3 to 1: 1.8.

8. A process according to claim 1 wherein said process is performed continuously.

9. A process according to claim 4 wherein said fraction is aliphatic and has 5 to 10 carbon atoms.

10. A process according to claim 1 wherein said water is separated by distillation.

11. In a process for the production of a primary amine by conversion at a first pressure of compounds containing carbonyl groups with ammonia to produce a reaction product and catalytic hydrogenation of said reaction product in the presence of a catalyst, wherein the catalyst contains cobalt, nickel, or a mixture thereof, the improvement which consists essentially of reacting said compounds with ammonia at a temperature of between about 15° C. and 80° C. at a pressure of between about 1 and 15 atmospheres, separating the water formed during the reaction from said reaction product and hydrogenating said product under a second pressure, said second pressure being greater than said first pressure.

* * * * *